United States Patent [19]

Zeelen et al.

[11] 4,221,713
[45] Sep. 9, 1980

[54] CYCLISATION SUBSTRATES AND RELATED 11α-EQUATORIALLY-SUBSTITUTED STEROIDS

[75] Inventors: Filippus J. Zeelen, Heesch; Marinus B. Groen, Schayk, both of Netherlands

[73] Assignee: Akzona Incorporated, Asheville, N.C.

[21] Appl. No.: 953,789

[22] Filed: Oct. 23, 1978

[30] Foreign Application Priority Data

Oct. 25, 1977 [NL] Netherlands .......................... 7711666

[51] Int. Cl.$^3$ ........................... C07J 5/00; C07C 5/09; C07J 71/00; C07C 39/18
[52] U.S. Cl. ..................... 260/239.55 R; 260/397.45; 260/397.5; 568/633; 260/346.11; 260/340.9 AS; 568/312; 568/322; 568/330
[58] Field of Search .......................... 260/397.5, 239.55

[56] References Cited

FOREIGN PATENT DOCUMENTS 1448873 9/1976 United Kingdom ........... 260/239.55 R

OTHER PUBLICATIONS

Journal of the American Chemical Soc. Feb. 18, 1976 pp. 1038–1041.

Primary Examiner—Elbert L. Roberts
Attorney, Agent, or Firm—Robert H. Falk; Charles A. Wendel; Francis W. Young

[57] ABSTRACT

Cyclisation substrates are disclosed of the formula:

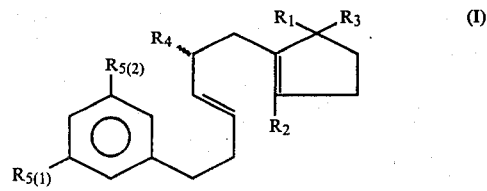

wherein:
(a) $R_1$ is H or alkyl of one to four carbon atoms;
(b) $R_2$ is H or alkyl of one to four carbon atoms, with the proviso that $R_1$ is H when $R_2$ is alkyl, and with the proviso that $R_2$ is H when $R_1$ is alkyl;
(c) $R_3$ is a suitable leaving group selected from the group consisting of hydroxy, alkoxy of one to four carbons, alkoxyalkoxy of two to four carbons, acyloxy of one to about seven carbon atoms, and trialkylsilyloxy of less than fifteen carbons;
(d) $R_4$ is methyl; and
(e) $R_{5(1)}$ and $R_{5(2)}$ are each H, alkyl of one to eight carbons, or an optionally esterified or etherified hydroxy group selected from the group consisting of hydroxy, alkoxy of one to four carbons, alkoxyalkoxy of two to four carbons, trialkylsilyloxy of one to fifteen carbons, cycloalkoxy of four to eight carbons, carboxyacyloxy of one to seven carbons or heterocyclic ether of five to seven atoms and four to six carbons, with the proviso that at least one of $R_{5(1)}$ and $R_{5(2)}$ is hydrogen.

A method is disclosed for the cyclisation of the compounds of formula I leading to compounds of the following formulae:

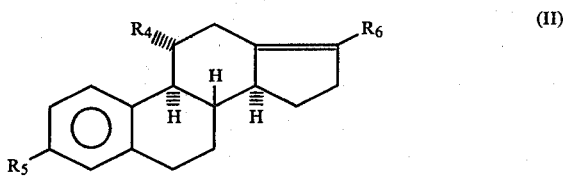

"para"

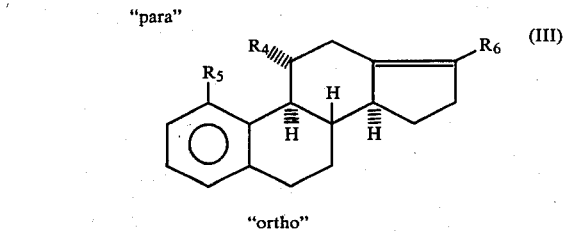

"ortho"

having $R_4$ and $R_5$ (one of $R_{5(1)}$ and $R_{5(2)}$ that may or may not be hydrogen) as defined above, with $R_6$ being alkyl of from one to about four carbon atoms.

20 Claims, No Drawings

CYCLIZATION SUBSTRATES AND RELATED 11α-EQUATORIALLY-SUBSTITUTED STEROIDS

BACKGROUND OF THE INVENTION

1. Field of the Invention

The invention relates to the preparation of novel cyclisation substrates for steroidal compounds, and also relates to the conversion of these cyclisation substrates substrates into novel steroidal compounds, in particular, 11α-substituted steroids of the oestrane series.

2. Related Applications

This application is related to Ser. No. 880,151, filed Feb. 22, 1978, to Ser. No. 880,153, filed Feb. 22, 1978, issued on Dec. 4, 1979, as U.S. Pat. No. 4,177,197 and to an application entitled "CYCLISATION SUBSTRATES AND RELATED 11β-AXIALLY SUBSTITUTED STEROIDS" Ser. No. 953,790, filed Oct. 23, 1978.

3. Prior Art and Other Information

The 11α-alkyl-19-nor-steroids are biologically active compounds to which access by synthetic routes is difficult for those in the art. For example, in 41 J. ORG. CHEM 531 (1976), an unsuccessful attempt is described to prepare 11-alkyl-substituted steroids by a total synthesis according to the method of Torgov. The cyclisation by the Johnson method of 2-(5'7'-dimethyl-trideca 3'(E),7'(E)-dien-11-ynyl)-3-methyl-cyclopent-2-enol to 11-methyl-steroids is described in the dissertation of T. M. Yarnell, (Stanford University, July 1975, in DISSERTATION ABSTRACTS INTERN, B 36 (1976) no. 10 at page 5054. The 5'-methyl group in the cyclisation substrate is the "pro-C-11" substituent. In this cyclisation, in addition to a range of other products, the 11α-methyl-steroid and the 11β-methyl-isomer were shown to be formed in approximately equal proportions. Stereo-selectivity was described as absent, and this synthesis therefore had little practical value.

Also, Johnson discloses in U.S. Pat. No. 4,032,579 various cyclopentenyl alcohols which can be cyclized to 11-chalcogen-substituted steroids (see especially col. 17, line 64 to col. 20, line 12), although there is no disclosure of an A-ring intermediate. Hughes (U.S. Pat. Nos. 3,417,105 and 3,547,909) disclose aryl cyclopentanediones which are cyclized to gonene compounds. Bertin et al (U.S. Pat. No. 3,526,648) and Bucourt (U.S. Pat. No. 3,906,096 discloses 11β-alkoxy steroids.

Of interest also is U.S. Pat. No. 3,778,434 to Coombs, directed to the preparation of 9α,11-dimethyl-substituted estranes from the corresponding estane-17-ones.

The stereospecific cyclisation of a compound of formula XX:

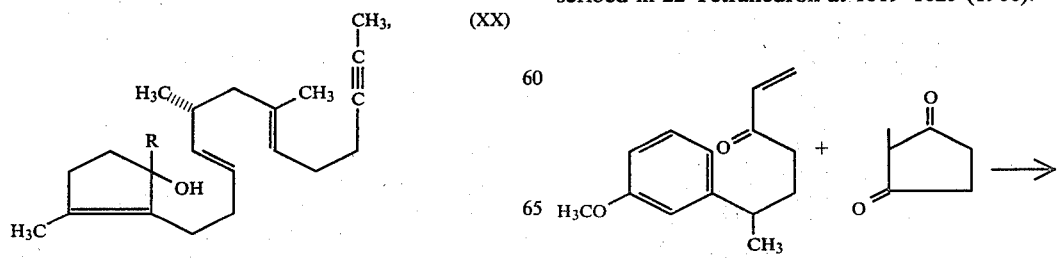

where R=CH₃ into a compound of formula XXI:

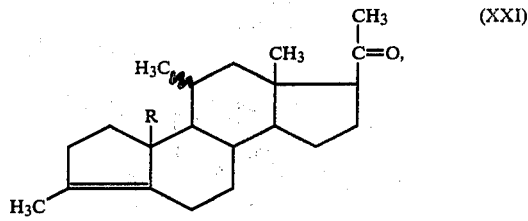

where R=CH₃ is described in 98 J.A.C.S. 1038 (1976).

Only the equatorial 11α-methyl derivative is formed. The cyclisation of a (pro)-11-hydroxy compound also results exclusively in the 11α-hydroxy steroid (98 J.A.C.S. 1038–1039 1976)).

Again it is mentioned that when this cyclisation is performed in the (pro)-19-nor-series (R is H), it proves that no stereo-selectivity occurs (see T. M. Yarnell, Dissertion, Stanford University, July 1975, in 1976 DISSERTATION ABSTRACTS INTERN, 1976, B35 no. 10, page 505 4). A mixture 11α- and 11β-substituted steroids in molar proportions of about 1:1 is formed.

Distantly related compounds by structure (7-substituted compounds) to those of formulae II–III of the instant invention are disclosed in Anner et al, U.S. Pat. No. 3,660,435 (7α-methyl-3,16α,17α-trihydroxy-$\Delta^{1,3,5(10)}$-oestratrienes for controlling fertility) and U.S. Pat. No. 3,804,866 (3-cyclopentyl ether of 7α-methyl-3,16α,17α,β-trihydroxy-$\Delta^{1,3,5(10)}$ oestratrienes and their 16,17-diacetates for controlling fertility. See also U.S. Pat. No. 3,345,570 (to Anner et al (isolation of 7α-methyl-3-oxo-$\Delta^4$ steroids from mixtures of the epimeric 7-methyl-compounds); U.S. Pat. No. 3,627,894 to Babcock (novel 7α-methylestrones); U.S. Pat. No. 3,928,398 to Grunwell et al (7αmethylestr-4-ene-3α,17β-diols as antiprogestational and antifertility agents); U.S. Pat. No. 3,574,197 (1-hydroxy-7α-methylestranes); U.S. Pat. No. 3,944,576 (7α-methoxymethylestranes); and U.S. Pat. Nos. 3,318,925/26/27/28/29 (7α-methyl-$\Delta^{1,3,5(10)}$-estratrienes).

A method of producing analogues of the compounds (II, III) unsubstituted in ring C, is disclosed in British Pat. No. 1,448,873 (producing oestrone by cyclizing 2-[(E)-6-aryl-3hexenyl]cyclopentenols of which the hexenyl group has not been substituted).

See also 95 J.A.C.S. 7501–7504 (1973).

The following stereo-selective synthesis was described in 22 Tetrahedron at 1019–1025 (1966):

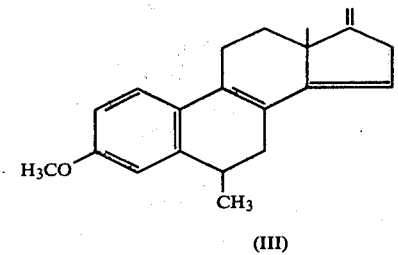

(III)

The main product obtained was the 6β-methyl compound (yield 25%–40% by weight) in addition to traces of the 6α-methyl compound. Since the 6α-methyl compounds are the most valuable, attempts were made to isomerise the 6β-methyl compounds to 6α-methyl compounds, after the A-ring had been converted to a 3-oxo-Δ⁴-system:

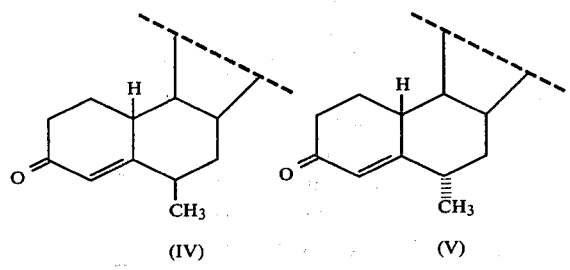

(IV)    (V)

This isomerisation occurs only in part, and the 6α-methyl compound can only be obtained in low yield by this route. The circuitous route via the enol acetate gives higher yields (see 90 Recueil 849 (1971)).

Other distantly related art by structure (6-substituted) includes U.S. Pat. No. 3,137,689 to Dorfmann et al, which teaches preparation of 6α-methyl-pregnenolones (antiovulatory activity); U.S. Pat. No. 3,257,427 to Bowers for 6-alkyl-3-desoxy-$\Delta^{1,3,5(10)}$ estratriene substituted in the 17 position by keto or hydroxy (anti-androgenic action, low feminizing effects; for fertility control and menstrual disorders); U.S. Pat. No. 3,816,481 to Douglas et al for 6α-methyl-4-gonenes (progestational activity); and British Pat. No. 1,448,873 (cyclisation of (arylhexenyl)-cyclopentenols to $\Delta^{1,3,5(10),13(17)}$ gonatetraenes unsubstituted in position 6).

SUMMARY OF THE INVENTION

Novel cyclisation substrates are disclosed of the formula:

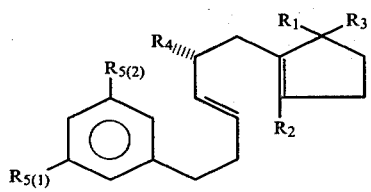

(I)

wherein:

(a) $R_1$ is H or alkyl of one to four carbon atoms;

(b) $R_2$ is H or alkyl of one to four carbon atoms, with the proviso that $R_1$ is H when $R_2$ is alkyl, and with the proviso that $R_2$ is H when $R_1$ is alkyl;

(c) $R_3$ is a suitable leaving group selected from the group consisting of hydroxy, alkoxy of one to four carbons, alkoxyalkoxy of two to four carbons, acyloxy of one to about seven carbon atoms, and trialkylsilyloxy of less than fifteen carbons;

(d) $R_4$ is hydrocarbyl of one to four carbons; and (e) $R_{5(1)}$ and $R_{5(2)}$ are each H, alkyl of one to eight carbons, or an optionally esterified or etherified hydroxy group selected from the group consisting of hydroxy, alkoxy of one to four carbons, alkoxyalkoxy of two to four carbons, trialkylsilyloxy of one to fifteen carbons, carboxyacyloxy of one to seven carbons, cycloalkoxy of four to eight carbons, or heterocyclic ether of five to seven atoms and four to six carbons, with the proviso that at least one of $R_{5(1)}$ and $R_{5(2)}$ is H.

Surprisingly, it has now been found that the cyclisation of a cyclisation substrate of formula (I):

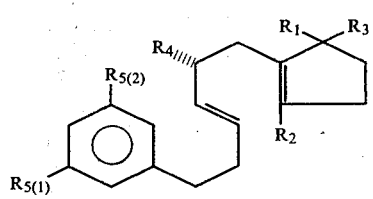

(I)

leads stereoselectively to equatorially-substituted steroid compounds of formulae II and III having $R_4$ and $R_5$ (one of $R_{5(1)}$ or $R_{5(2)}$ which may or may not be hyrogen) as described above:

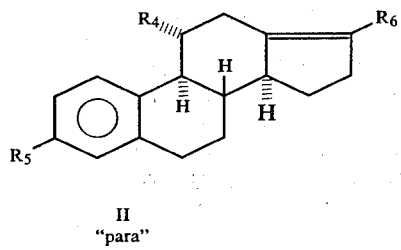

II
"para"

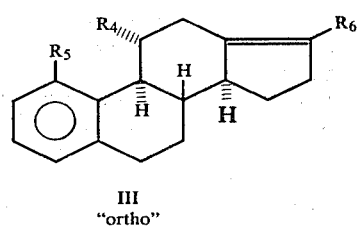

III
"ortho"

which may be represented in shorthand notation by the following formula (positions indicated in small arabic numerals):

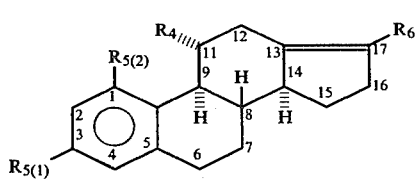

(II–III)

which is more recognizable by those in the art. $R_6$ is an alkyl moiety of one to four carbon atoms.

In formulae I, II and III, most preferably $R_1$ and $R_2$ are H or CH₃, $R_3$ is OH, $R_4$ is CH₃, one of $R_{5(1)}$ and $R_{5(2)}$ is hydrogen and the other OCH₃ or trialkylsilyloxy of three to twelve carbon atoms, and $R_6$ is CH₃.

When $R_{5(1)}$ is $R_{5(2)}$, the resultant compounds are of course identical, but when $R_{5(1)}$ is not $R_{5(2)}$, two isomers result from the cyclisation; the proportions of which are strongly influenced by the cyclisation conditions and the choice of the substituents $R_{5(1)}$ and $R_{5(2)}$.

DESCRIPTION OF THE PREFERRED EMBODIMENTS

The cyclisation substrates of structure I are novel compounds which may be prepared in several ways, the individual steps of each way being known to those skilled in the art. The invention is therefore characterized by the preparation of novel compounds with the general formula I by steps which are in themselves known to those in the art. The invention is also characterized by the cyclisation of the novel cyclisation substrates of formula I to the novel and biologically active steroid compounds substituted equatorially in position 11, with the structures II and III.

Referring to the Flow Diagram below, the cyclisation substrate I may, for example, be prepared by condensing in Reaction (or Step) (a) an 8-$R_2$-2-$R_4$-5,5,8,8-tetra-alkoxy-(or -alkylene-dioxy)-octanal (V) with a 3-aryl-propylidene-triaryl-phosphorane (Wittig reagent IV), or by condensing an 8-$R_2$-2-$R_4$-5,5,8,8-tetra-alkoxy-(or -alkylene-dioxy)-octylidene-tri-arylphosphorane (V) with a 3-aryl-propanal (IV) under conditions which favor the (E)-configuration (Wittig-Schlosser reaction, see for example the German Pat. Specifications Nos. 1,270,545 and 1,279,678, and 5 ANGEW CHEMIE, Int. Ed. (1966) 126. Instead of the tetra-alkoxy or alkylene-dioxy reagent, use may also be made of the thio analogues known to those in the art.

The (E)-olefine-bis-ketal (VI) obtained is hydrolysed in step (b) under weakly acid conditions to a 1-aryl-5-$R_4$-8,11-dioxo-11-$R_2$-3-undecene (VII), after which the dioxo compound (VII) is condensed to give a 2-(2'-$R_4$-6'-aryl-3'-hexenyl)-3-$R_2$-2-cyclopentenone (VIII) (Step (c)).

In step (d), if $R_2$ is alkyl of one to four carbons, the ketone obtained is reduced to an alcohol; and when $R_2$ is H, the ketone is reacted with a compound $R_1Li$ or $R_1Mg$-halogen (where $R_1$ is alkyl of one to four carbons) giving a teritiary alcohol. The OH-group is optionally further esterified or converted to an ether in ways known to those in the art.

The cyclisation substrate (I) obtained in Reaction (d) is subsequently cyclised with a Lewis acid under suitable acid conditions, giving a tetracyclic compound with an equitorial $R_4$-substituent.

The preparation indicated above is summarized by the following reaction scheme:

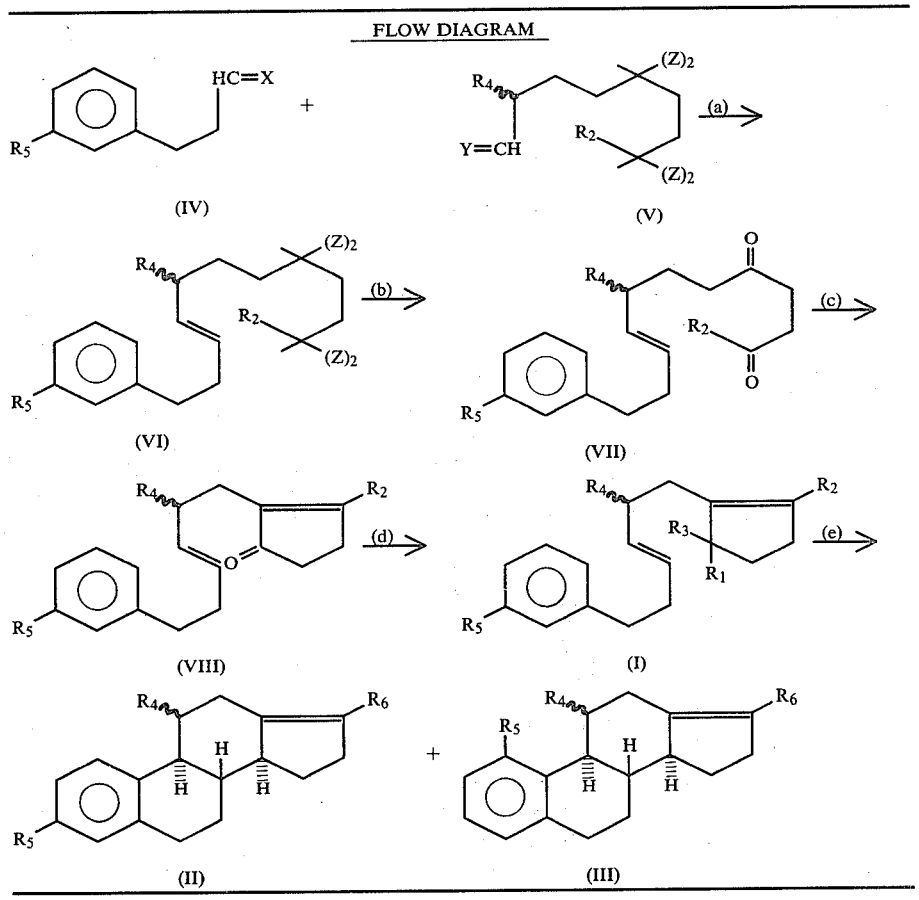

FLOW DIAGRAM

In this Flow Diagram, $R_1$, $R_2$, $R_3$, $R_4$, $R_5$ and $R_6$ have the meanings already assigned above. X is O or $P(R_7)_3$, where $R_7$ is an aryl hydrocarbon residue with 6 or 7 carbon atoms and is a preferably phenyl; Y is O or $P(R_7)_3$, where $R_7$ has the meaning assigned above, with the proviso that Y is O when X is $P(R_7)_3$ and vice versa. Z is an alkyl-chalcogen group, that is: alkoxy or alkylthio, each with one to four carbon atoms, preferably one to two carbon atoms. Preferably, $(Z)_2$ is an alkylene-dichalcogen group, that is: alkylene-dioxy or alkylene-dithio, with two to three carbon atoms, for example ethylene dioxy.

For the preparation of the dioxo compound with the structure VII, it is also possible to react a 2-R$_4$-4-(5'-R$_2$-2'-furyl)-butanal (X) with a phosphorane of formula IV (X is P(R)), or a 2-R$_4$-4-(5'-R$_2$-2'-furyl)-butylidene-triaryl-phosphorane with an aldehyde of formula IX (X is O), by the Wittig-Schlosser reaction, giving a furyl-(E)-olefine (X), according to the reaction scheme:

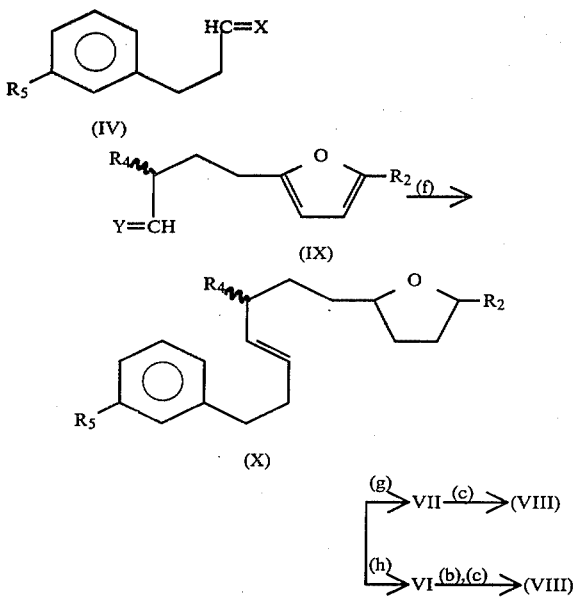

after which the furyl-(E)-olefine of formula (X) obtained is hydrolysed (step g) to the dioxo compound of formula VII. This last hydrolysis may constitute a problem, since the reaction is difficult and the keto-aldehyde of formula VII (R$_2$ is H) obtained is not very stable. In this case, a preferred method (step h) constitutes opening of the furan ring in the furyl-(E)-olefine with the aid of a suitable strong acid known to those in the art for reactions of this type, for example p-toluene-sulphonic acid, in the presence of a ketal-forming agent known to those in the art, for example glycol, such that a ketal-acetal of formula VI (R$_2$=H) is obtained which can then be converted in the way indicated above into a cyclisation substrate.

With respect to the substituents R$_1$ to R$_6$ inclusive, the following may further be noted;

R$_1$ or R$_2$ is generally methyl or ethyl, preferably methyl, whereby the other substituent is then H. R$_3$ as a suitable "leaving" group known to those in the art is generally alkoxy of one to four carbons, for example methoxy; otherwise (1) alkoxyalkoxy of two to four carbons, for example methoxymethoxy or 1'-ethoxymethoxy; (2) carboxyacyloxy of one to seven carbons, for example acetoxy, propionyloxy, butyroxy, pivaloyloxy, valeryloxy, benzoyloxy; or (3) trialkylsiloxy of less than fifteen carbons, for example, trimethylsilyloxy.

R$_4$ is a hydrocarbyl (hydrocarbon) group of one to four carbon atoms, where hydrocarbyl is understood to mean: a monovalent radical consisting of hydrogen and carbon atoms and which is a saturated or unsaturated aliphatic or alicyclic residue.

Examples of hydrocarbyl groups for R$_4$ are: methyl, ethyl, isopropyl, cyclopropyl, butyl, allyl, propargyl. R$_4$ is preferably methyl.

One of R$_{5(1)}$ and R$_{5(2)}$ is hydrogen and the other ("active" R$_5$ moiety) is preferably hydroxy, or in the alternative, optionally etherified or esterified hydroxy of less than ten carbon atoms; for example, (1) hydrocarbyloxy of one to eight carbons such as methoxy, ethoxy, cyclopentoxy, cyclohexenyloxy, benzyloxy; (2) α-alkoxyalkoxy of two to four carbons, such as methoxymethoxy, α-ethoxyethoxy; (3) trimethylsilyloxy or tetrahydropyranyloxy; and (4) carboxyacyloxy of one to seven carbons, such as acetoxy, pivaloyloxy or benzoyloxy.

The active R$_5$ moiety may be heterocyclic ether wherein the heterocyclic member has five to seven atoms, is monoheterocyclic (one non-carbon member in the ring) or diheterocyclic (two non-carbon members) and has from four to six carbon atoms, and is unsubstituted.

If the active R$_5$ moiety is an oxy group, then the positions 2, 4 and 6 of the phenyl nucleus are activated in the cyclisation. Due to steric factors, position 4 takes no part in the reaction, and for the case R$_{5(1)}$ is not equal to R$_{5(2)}$, two products may therefore be formed as indicated above by the formulae II and III. As previously noted, the ratio of formation of these two products can be changed considerably in favor of one thereof by a suitable choice of R$_{5(1)}$ and/or R$_{5(2)}$. If R$_{5(1)}$ is, for example, trimethylsilyloxy and R$_{5(2)}$ is H, then much more "para" (position 6) product is formed than "ortho" (position 2) product.

If use is made as starting material of a phosphorane with R$_{5(1)}$ and/or R$_{5(2)}$ being a protected hydroxy group, then the protective group may remain intact during the various reaction steps, but it may also undergo modification. Certain protective groups known to those in the art are preferred for some reaction steps, while again other protective groups are preferred for other reaction steps. In the steps (a) and (b), for example, R$_{5(1)}$ and/or R$_{5(2)}$ is preferably methoxy or methoxymethoxy. In steps (c) and (d), R$_{5(1)}$ and/or R$_{5(2)}$ may without objection by hydroxy, while in step (e) R$_{5(1)}$ a and/or R$_{5(2)}$ is preferably trimethylsilyloxy if the interest is primarily for the "position 6" product. Specifically, the "para" product R$_{5(2)}$ is H) is most preferred since it may be used for the preparation of steroids similar to those occurring in nature.

The cyclisation substrate contains two asymetric centers, namely, the carbon atom carrying the substituent R$_1$ and the carbon atom with the substituent R$_4$. The stereochemistry of the cyclisation product proves to be governed predominantly by the latter center in the cyclisation product. The substituent R$_4$ surprisingly proves to occur predominantly in the equatorial configuration.

If use is made of a racemic cyclisation substrate as starting material, i.e., a material with nearly equal amounts of the (R)-R$_4$-substituted and the (S)-R$_4$-substituted compounds, then a racemic tetracyclic product is formed, consisting of 2 enantiomers is shown to be formed, while on grounds of the two asymmetric centers, without optical induction, four stereoisomers in equal amounts would be formed. That the chiral center with the substituent R$_1$ has little, if any, influence on the stereochemistry of the end-product may be proved by the fact that the (S)-R$_1$-(R)-R$_4$-substituted cyclisation substrate gives the same R$_4$-equatorially-substituted cyclisation product as the (R)-R$_1$-(R)-R$_4$-substituted cyclisation substrate. Thus, for example, both 1(S)-3-methyl-2-[2'(R)-methyl-6'-(m-methoxyphenyl)-3'(E)-hexenyl]-2-cyclo-pentenol and 1(R)-3-methyl-2-[2'(R)-methyl-6'-(m-methoxyphenyl)-3'(E)-hexenyl]-2-cyclopentenol give the natural 3-methoxy-11α-methyl-$\Delta^{1,3,5(10),13(17)}$-gonatetraene on cyclisation.

It has been indicated in formula I that the substituent $R_4$ may be present in the (R)-configuration or the (S)-configuration. If a racemate is used as starting material and the ortho/para isomerism of the aromatic ring is ignored, then a racemate of the $R_4$-equatorially substituted steroid compound with the structure II is formed in the cyclisation. If an optically active cyclisation substrate is used, for example the (R)-$R_4$-compound ($R_4$=$CH_3$), then an optically active compound of formula II is formed, that is, a "natural" 11α-$CH_3$-$\Delta^{1,3,5(10),13(17)}$-gonatetraene.

By epoxizing of this 13(17) olefine (II–III), preferably by conversion into a 13,17-halohydrin, preferably a chloro- or bromohydrin, and treatment of the halohydrin with a base, the corresponding 11α-$CH_3$-13α,17α-epoxy compound of formula XI below is formed (if the epoxidation is performed directly with a peracid, the 13β,17β-epoxy compound is formed). Opening the α-epoxide ring under weakly acid conditions, preferably by use of an aprotic Lewis acid, for example $BF_3$/diethyl ether, initiates migration of the substituent $R_6$ from the 17-position to the 13 position such that the corresponding 11α-$CH_3$-13β-$R_6$-17-ketone of formula XII is formed from the α-epoxide XI.

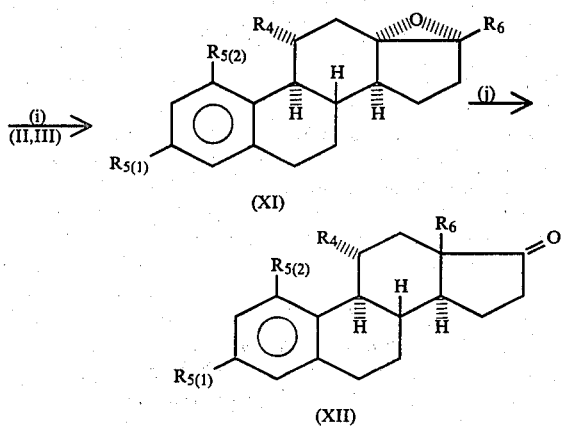

(The antipode can be converted into the ent-3-$R_5$-11α-$R_4$-13β-$R_6$-$\Delta^{1,3,5(10)}$-gonatrien-17-one in a corresponding fashion). When $R_{5(1)}$ is methoxy, $R_{5(2)}$ is hydrogen and $R_6$ is methyl, the 3-methyl ether of 11α-alkyl-oestrone is obtained in this way.

The internal condensation of the dioxo compound VII (Step (c)) may be brought about in the usual way, for example, with alkaline ethanol or with trimethylbenzyl-ammonium hydroxide.

In the cyclisation Reaction (step e), an effective amount of an aprotic or a protic Lewis acid is used and the reaction is performed in a non-nucleophilic protic or aprotic solvent. Examples of suitable solvents are formic acid, acetic acid, trifluoro-acetic acid, trifluoroethanol, benzene, saturated hydrocarbons such as pentane, hexane, cyclohexane, and halogenated hydrocarbons such as dichloromethane.

Examples of protic Lewis acids are carboxylic acids with a pK (20° C.) of less than about 4, and preferably less than about 2, such as, for example, trifluoro-acetic acid, trichloroacetic acid, formic acid.

Examples of aprotic Lewis acids are stannic chloride, titanium tetrachloride, zinc chloride, zinc bromide, boron trifluoride. Aprotic Lewis acids are stannic chloride, titanium tetrachloride, zinc chloride, zinc bromide, boron trifluoide. Aprotic Lewis acids are preferably used, in an amount of about 0.1 to about 10 moles per mole cyclisation substrate, and preferably about 0.5 to about 5 moles per mole. Stannic chloride is preferable.

The cyclisation reaction is usually carried out at a temperature below room temperature (about 20°–22° C.) and above −150° C., preferably at a temperature between about +10° C. and about −100° C.

The mixtures of "ortho"- and "para"- products ("ortho" means A-aromatic steroid substituted in position 1, "para" means A-aromatic steroid substituted in position 3) of compound II-III obtained in the cyclisation step (e) may be separated in the usual way known to those in the art, for example, by chromatochromatography or by crystallization. Racemates of intermediate or final products may be resolved to give the optical antipodes in the usual way.

The 11α-alkyl-$\Delta^{1,3,5(10),13(17)}$-gonatetraenes obtained in the cyclisation, and the 13α, 17α-epoxy compounds which can be prepared from these, are new. These compounds have hormonal properties and are furthermore of value as starting materials for known, biologically active 11α-alkyl steroids.

As to the reaction steps (a)–(e) the following additional information can be given:

Reaction step (a) is usually carried out at a temperature between about −100° C. and about 0° C., preferably between about −75° C. and about −25° C. The solvent is usually an etheric solvent, such as diethyl ether, tetrahydrofuran and mixtures thereof. A preferred solvent is an 1:1 mixture of diethyl ether and tetrahydrofuran.

Reaction step (b) is usually carried out at a temperature between about 20° C. and 80° C., preferably between about 50° C. and 60° C. The solvent may be an etheric solvent, such as dimethoxyethane, or a mixture of water and an alcohol, such as ethanol. An 1:2 mixture of water and ethanol containing between 5 and 10 mmol HCl per liter, is very suited.

Reaction step (c) is usually carried out between about 60° C. and 80° C., preferably at about 80° C. The solvent is the same as used in step (b). An 1:2 mixture of water and ethanol containing between 5 and 10 mmol NaOH or an equivalent amount of KOH or trimethylbenzyl-ammoniumhydroxide is very suited.

Reaction step (d): The reaction of the ketone to an alcohol is carried out with a complex metallic hydride, such as lithiumaluminiumhydride, di-isobutyl-aluminium-hydride, sodium-di-isobutylboronhydride, at a temperature between about −50° C. and 0° C., preferably between about −25° C. and 0° C. The reaction of the ketone with a compound $R_1Li$ or $R_1Mghalogen$ is usually carried out at a temperature between −70° C. and 0° C., preferably between −70° C. and −20° C. The solvent is usually an etheric solvent, preferably diethyl ether.

The reaction steps (a), (d), and (e) are preferably carried out in an inert atmosphere (nitrogen or argon blanket).

Reaction step (e): When using a protic solvent, preferably a protic Lewis acid is used. A protic solvent, such as formic acid, trifluoro-acetic acid, trifluoroethanol, may also serve as protic Lewis acid. An aprotic solvent may be combined with either a protic Lewis acid or an aprotic Lewis acid.

Although the invention has been described with reference to the specific embodiments about, numerous variations and modifications will become evident to those skilled in the art, without departing from the scope and spirit of the invention as described above, defined in the appended claims, and as shown in the following Examples:

EXAMPLE I 3-(m-methoxyphenyl)-propyl-triphenylphosphonium bromide (Precursor of Compound IV)

A solution of m-bromo-anisole (37.4 g, 0.2 mol) in dry tetrahydrofuran (200 ml) was added dropwise under nitrogen to magnesium shavings (4.8 g, 0.2 g.at.).

The solution obtained was stirred for about 1 hour at room temperature, after which it was added over a period of about 1.5 hours to a solution of 80.1 g (0.4 mol) 1,3-dibromopropane in 80 ml dry tetrafuran, which had been warmed to 50° C. under nitrogen. The mixture obtained was heated at 70° C. for 16 hours, cooled, and mixed with ether and an aqueous solution of ammonium sulphate. The organic layer was separated, dried over anhydrous sodium sulphate and distilled under vacuum. In this way, dibromopropane was recovered (48 g, room temperature 66°–67° C./18 mm) and 1-bromo-3-(m-methoxyphenyl)-propane (26.5 g, 58%, boiling point 85°–95° C./0.7 mm) was obtained.

The product was warmed for 8 hours at 120° C. with triphenylphosphine (40 g. 0.15 mol, 1–3 eq) and toluene (30 ml). Cooling gave a vitreous precipitate. This was dissolved in a minimum of boiling acetone, and precipitated by cooling and adding ether. 53 g (93% yield) of crystalline phosphonium salt was obtained, melting point 130°–134° C.

EXAMPLE II (Examples II–V are used to show a way of preparing Compound V)

Preparation of dl-2-methyl-5-(3-bromobutyl)furan

A solution of 4-(5-methyl-2-furyl)-butan-2-one (16 g, 0.5 mol) in methanol (750 ml) was cooled to the range of about 0°–5° C., after which 35 ml 0.1 N sodium hydroxide and 19 g (0.5 mol) sodium borohydride were added consecutively, the last in portions. The mixture was stirred for 1.5 hours, after which glacial acetic acid was added to obtain a pH of 7 (about 0.5 ml). The methanol was largely removed by distillation under vacuum. The residue was taken up in ether, washed with water, and dried over anhydrous magnesium sulphate. Removal of the solvent by evaporation gave 77 g (quantitative yield) dl-2-methyl-5-(3-hydroxybutyl)-furan.

This product was dissolved in a mixture of dichloromethane (750 ml) and pyridine (230 ml), and the resultant solution was cooled to −15° C. Methane-sulphonyl chloride (75 ml) was then added slowly dropwise with stirring. The mixture obtained was stirred for a further 2.5 hours at about 0° C. The reaction mixture was washed with 2 N hydrochloric acid until neutral, dried (anhydrous magnesium sulphate) and evaporated to dryness, giving in this way 112 g (93%) of the mesylate as an oil which was not purified. The mesylate was dissolved in dry dimethylformamide (900 ml), after which lithium bromide (192 g, 5 eq.) was added. The mixture was stirred under a nitrogen atmosphere at 60° C. for about 1 hour. It was then cooled, poured into water, and extracted with ether (6×100 ml). The ether extracts were washed with saturated sodium chloride solution, drid (anhydrous MgSO$_4$) and evaporated to dryness. The residue was distilled under vacuum. In this way, 78 g (77% yield) of the desired product was obtained, boiling point 61°–63° C./0.15 mm.

EXAMPLE III

Preparation of dl-8-bromo-2,5-bis(ethylene-dioxy)nonane

A mixture of dl-2-methyl-5-(3-bromobutyl)furan (44 g, 0.2 mol) from Example II, glycol (175 ml), dry tetrahydrofuran (175 ml), tri-ethyl orthoformate (70 ml) and p-toluene-sulphonic acid was heated at about 80° C. under nitrogen for 3 hours.

The reaction mixture was cooled, mixed with 0.2 N sodium hydroxide (350 ml) and extracted with ether. The extracts were dried over anhydrous MgSO$_4$ and evaporated to dryness. The residue was chromatographed on silica gel (600 g) with hexane/ethyl acetate, 8:2. The starting material (16.3 g, 37%) was eluted first, followed by the product (39 g, 60% yield; 96% based on converted starting material); oil, NMR (CDCl$_3$):δ1.30 (s, protons at C-1), 1.70 (s, protons at C-3 and C-4), 1.70 (d, J=6.5, $\underline{CH_3}$—CHBr), 3.93 (s, OCH$_2$CH$_2$O), 4.12 (m, CHBr).

EXAMPLE IV

Preparation of dl-2-methyl-5,8-bis(ethylene-dioxy)pelargononitrile

The bromide from example III (32.3 g, 0.1 mol) was dissolved in dry dimethylsulphoxide (250 ml), powered potassium cyanide was added, and the mixture obtained was stirred at about 60° C. under nitrogen for 4 hours.

The reaction mixture was cooled, mixed with water, and extracted with ether. The extracts were washed with water, dried over anhydrous MgSO$_4$ and evaporated to dryness. The residue was chromatographed on silica gel with hexane/ethyl acetate 60:40. The product was obtained as a colorless oil (22.7 g, 85% yield), NMR (CDCl$_3$):δ1.31 (s, protons at C-9+d, J=7, $\underline{CH_3}$CH), 1.70 (m), 2.65 (q, J=7, $\underline{CH}$CN), 3.94 (s, OCH$_2$CH$_2$O).

EXAMPLE V

Preparation of dl-2-methyl-5,8-bis(ethylene-dioxy)nonanal (formula V, R$_2$=methyl; R$_4$=methyl; (Z)$_2$=ethylene-dioxy; Y=O The nitrile from example IV (13.5 g, 0.05 mol) was dissolved in dry toluene (250 ml) and cooled under nitrogen to about −78° C. Diisobutyl aluminium hydride (50 ml of a 1.2 M solution in toluene, 0.06 mol) was then added dropwise such that the temperatue did not rise above about −70° C.

After stirring for a further 10 minutes, water (10 ml) was cautiously added and the mixture thus obtained was slowly warmed to room temperature. Anhydrous Na$_2$SO$_4$ and HYFLO TM were added, and the mixture thus obtained was filtered over a layer of HYFLO TM. The filter-cake was washed with ether. The combined filtrates were evaporated to dryness and the residue was chromatographed on silica gel with hexane/ethyl acetate 70:30, giving the aldehyde as a colorless oil (13.4 g, 98% yield), NMR (CDCl$_3$):δ1.09 (d, J=7, $\underline{CH_3}$—CH), 1.30 (s, protons at C-9), 1.70 (s, protons at C-6 and C-7), 2.33 (m, CHCHO), 3.93 (s, OCH₂CH₂O), 9.61 (d, J=1.5, CHO).

EXAMPLE VI—Step (a)

Preparation of dl-(E)-1-(m-methoxyphenyl)-5-methyl-8,11-bis(ethylenedioxy)-3-dodecene (Formula VI, $R_2$=methyl; $R_4$=methyl; $R_5$=methoxy; $(Z)_2$=ethylene-dioxy)

Phenyl-lithium in ether (50 ml of a 1.1 M solution, 0.055 mol) was added dropwise under nitrogen to a stirred suspension of 3-(m-methoxy-phenyl)-propyl-triphenylphosphonium bromide (27 g, 0.055 mol) in dry tetrahydrofuran (125 ml), cooled in ice. The orange-red mixture obtained was stirred for a further 15 minutes without cooling, after which it was cooled to about −70° C. The aldehyde of Example V (13.6 g, 0.05 mol), dissolved in dry tetrahydrofuran (25 ml), was added dropwise after which the whole was stirred for 5 minutes at −70° C. A further amount of phenyllithium in ether (90 ml, 1.1 M, 0.10 mol) was added and the red solution obtained was warmed to about −30° C. After about 15 minutes at −30° C., the reaction mixture was poured into water and extracted with ether. The ether extracts were dried (anhydrous Na₂SO₄), filtered and evaporated to dryness. The residue was chromatographed on silica gel (400 g) with hexane/ethyl acetate 80:20, followed by 60:40 by weight mixture hexane/ethyl acetate and pure ethyl acetate. The desired product (8.4 g, 42% yield) was eluted first, followed by the aldehyde (8 g, 59%) used as starting material. Product: oil, NMR (CDCl₃):δ0.95 (d, J=6.5, CH₃CH), 1.30 (s, protons at C-12), 1.70 (s, protons at C-9 and C-10), 3.78 (s, CH₃O), 3.92 (s, OCH₂CH₂O), 5.36 (m, CH=CH).

EXAMPLE VII—Steps (b) and (c)

Preparation of dl-3-methyl-2[(E)-6'-(m-methoxyphenyl)-2'-methyl-3'-hexenyl]-2-cyclopentenone (Formula VIII, $R_2$=methyl; $R_4$=methyl; $R_5$=methoxy)

(a) A solution of the Wittig product from Example VI (8.1 g, 0.02 mol) in 95% ethanol (200 ml) and 0.2 N hydrochloric acid (100 ml) was heated for 2 hours at 50°–55° C., giving the product of formula VII ($R_2$, $R_4$, $R_5$ as before).

(b) 20 ml 2 N potassiumhydroxide solution and 180 ml 95% ethanol were then added, and the solution obtained was boiled under reflux for 5 hours. The reaction mixture was evaporated under vacuum to a volume of about 100 ml and then extracted with ethyl acetate. The extracts were dried (anhydrous Na₂SO₄) and evaporated to dryness. The residue was chromatographed on 150 g silica gel with hexane/ethyl acetate 90:10. The product was obtained as a colorless oil (5.3 g, 89% yield). NMR (CDCl₃):δ0.93 (d, J=6, CH₃CH), 1.99 (s, CH₃C=C), 3.78 (s, CH₃O), 5.31 (m, CH=CH).

EXAMPLE VIII—Step (d)

Preparation of dl-3-methyl-2-[(E)-6'-(m-methoxyphenyl)-2'-methyl-3'-hexenyl]-2-cyclopentenol (Formula I, $R_1$=H; $R_2$=methyl; $R_3$=hydroxy; $R_4$=methyl; $R_5$=methoxy)

Lithium aluminium hydride (0.57 g, 0.015 mol) was slowly added at about −20° C. to a solution of the cyclopentenone from Example VII (3.0 g, 0.01 mol) in dry ether (100 ml). The mixture was warmed with stirring to about 0° C. over a period of about 30 minutes. The excess hydride was decomposed by cautious addition of saturated sodium sulphate solution. The ether layer was decanted from the resultant suspension which was further extracted two times with portions of dry ether.

The combined ether solutions were evaporated to dryness under vacuum in a cold waterbath (less than or about 20° C.), giving 3.0 g product (99% yield) in the form of a colorless oil, NMR (CDCl₃+C₅D₅N):δ0.88 and 0.98 (2×d, J=6, CH₃CH), 1.60 (s, CH₃C=C), 3.76 (s, CH₃O), 4.46 (m, H—C—OH), 5.30 (m, CH=CH).

EXAMPLE IX—Step (e), Cyclisation

Preparation of dl-1- and 3-methoxy-11α, 17-dimethyl-Δ$^{1,3,5(10),13(17)}$-gonatetraene (formulae II and III, $R_4$=methyl; $R_5$=methoxy; $R_6$=methyl)

A solution of stannic chloride (10.5 g, 0.04 mol) in 280 ml dry di-chloromethane was cooled under nitrogen to about −100° C. (via acetone/liquid nitrogen). The cyclopentenol from Example VIII (93.0 g, 0.01 mol), dissolved in 20 ml dry dichloromethane was then added dropwise over a period of about 1 hour. After stirring for a further 20 minutes, the reaction was halted by slowly adding 90 ml of a 5% solution of KOH in methanol (temp. less than about −85° C.). The mixture obtained was slowly warmed to about 20° C., washed with water and dried over anhydrous potassium carbonate. The solvent was removed by evaporation and the residue was chromatographed on 60 g silica gel with hexane/toluene 90:10 by weight followed by hexane/toluene 80:20 by weight. The 1-methoxy-isomer was eluted first (0.485 g, 17% yield), consisting for 92% of the 11α-methyl derivative. The pure compound had a melting point of 80° C. after crystallization from methanol. The 3-methoxy-isomer was subsequently eluted (1.34 g, 50% yield). This fraction was then chromatographed on silica gel (140 g) impregnated with 20% silver nitrate, with hexane/toluene 80:20 by weight. In this way, the pure 11α-methyl-isomer was obtained (1.01 g, 36% yield), melting point 98°–99° C. (from pentane). The 11β-methyl-isomer was also isolated in the form of an oil (0.157 g, 5.5% yield).

EXAMPLE X

Preparation of dl-11α-methyloestrone, methyl ether (Formula XII, $R_4$=CH₃, $R_{5(1)}$=CH₃O, $R_{5(2)}$=H, $R_6$=CH₃)

A solution of 3-methoxy-11α-methyl-17-methyl-Δ$^{1,3,5(10),13(17)}$-gonatetraene (0.282 g, 0.001 mol) in t-butanol/water 2:1 (20 ml) was cooled in ice. N-chlorosuccinimide (0.265 g, 0.002 mol) was added to the suspension thus obtained, after which the whole was stirred for about 1 hour at room temperature. Sodium bisulphite (0.10 g) and 5 ml 40% KOH solution were then added consecutively and the whole was stirred for about 30 minutes at room temperature (20°–25° C.). Hexane (50 ml) was added and the resultant aqueous layer was removed. The organic layer was evaporated to dryness under vacuum.

The residue, consisting of the 13α, 17α-epoxy derivative, was taken up in toluene (20 ml) and treated with boron trifluoride etherate (0.2 ml) for 1 minute at room temperature. The dark red reaction mixture was diluted with ether and shaken with saturated sodium bicarbonate solution. The organic layer was separated, dried over anhydrous $Na_2SO_4$, and evaporated to dryness. The residue was chromatographed on 30 g silica gel with hexane/ethyl acetate 9:1.

The material obtained was crystallized from ether/pentane, giving 54 mg (18% yield) product, m.p. 88°–90° C.

EXAMPLE XI

Preparation of dl-2-methyl-4-(2-furyl)butyronitrile (Precursor of Formula IX, $R_2=H$, $R_4=CH_3$)

Methylvinylketone (14 g, 0.2 mol) was added dropwise over a period of about 2 hours to furan (150 ml), containing a trace of p-toluene-sulphonic acid, boiling under reflux. The dark brown reaction mixture was stirred for about 16 hours at room temperature. The excess furan was removed by distillation, after which the residue was distilled under vacuum giving 4-(2-furyl)butan-2-one (18.5 g, 67% yield). In a way analogous to that described in Example II, the ketone was reduced to the corresponding alcohol and subsequently converted to the mesylate (28 g, 92% yield).

The mesylate (22.8 g, 0.1 mol) was dissolved in dry DMSO (100 ml). Potassium cyanide (13 g, 0.2 mol) was added and mixed, and the mixture obtained was heated at about 70° C. under nitrogen for about 16 hours.

The reaction mixture was poured into water and extracted with ether (4 times, each with 200 ml ether). The ether extracts were washed with water, dried (anhydrous $Na_2SO_4$) and evaporated to dryness. The residue was chromatographed on silica gel with hexane/ethyl acetate 80:20 by weight, giving the pure product as a colorless oil (10.5 g, 70% yield), b.p. 75°–76° C./2 mm.

EXAMPLE XII

Preparation of dl-2-methyl-4-(2-furyl)butanal (formula IX, $R_2=H$; $R_4=$methyl; $Y=O$)

In a way analogous to that described in Example V, the nitrile of Example XI was reduced to the corresponding aldehyde. The crude product was chromatographed on silica gel with hexane/ethyl acetate 80:20 by weight, giving the pure aldehyde in 58% yield, b.p. 71°–72° C./18 mm.

EXAMPLE XIII—Step (f)

Preparation of dl-(E)-1-(2-furyl)-3-methyl-7-(m-methoxyphenyl)-4-heptene (Formula X, $R_2=H$; $R_4=$methyl; $R_5=$methoxy)

The aldehyde from Example XII (1.52 g, 0.010 mol) was reacted with 3-(m-methoxyphenyl)-propyl-triphenylphosphonium bromide (5.4 g, 0.011 mol) in an exact way analogous to that described in Example VI.

The crude product was chromatographed on silica gel with a hexane/ethyl acetate 95:5 by weight solution, giving the pure product as a colorless oil (2.65 g, 93% yield). NMR ($CDCl_3$): δ0.97 (d, J=6, $\underline{CH_3}$CH), 3.77 (s, $CH_3O$), 5.35 (m, CH=CH), 5.92 (m), 6.25 (m) and 7.27 (m, furan protons).

EXAMPLE XIV—Step (h)

Preparation of dl-(E)-1-(m-methoxyphenyl)-5-methyl-8,11-bis(ethylene dioxy)-3-undecene (Formula VI, $R_2=H$; $R_4=$methyl; $R_5=$methoxy; $(Z)_2=$ethylene-dioxy)

The Wittig product from Example XIII (0.284 g, 0.001 mol) was mixed with dry benzene (5 ml), glycol (5 ml) and p-toluene-sulphonic acid (0.50 g). This mixture was boiled under nitrogen with vigorous stirring for 2 weeks. The reaction mixture was neutralized with a few drops 0.2 N sodium hydroxide and mixed with water and ether. The organic layer was separated, dried over anhydrous $MgSO_4$ and evaporated to dryness. The residue was chromatographed on silica gel with hexane/ethyl acetate 80:20. The product was obtained as a colorless oil (0.298 g, 77% yield.) NMR ($CDCl_3$): δ0.95 (d, J=6, $\underline{CH_3}$CH), 3.77 (s, $CH_3O$), 5.35 (m, trans-CH=CH), 7.20 (m, proton at C-3).

EXAMPLE XV—Steps (b), (c)

Preparation of dl-2[(E)-6'-(m-methoxyphenyl)-2'-methyl-3'-hexenyl]-2-cyclopentenone (Formula VIII, $R_2=H$; $R_4=$methyl; $R_5=$methoxy)

The product from Example XIV (0.30 g, 0.77 mol) was dissolved in a mixture of dimethoxyethane (20 ml) and 1 N hydrochloric acid (7 ml). The solution was heated at about 50° C. under nitrogen for about 3 hours. The reaction mixture was diluted with water and extracted with ethyl acetate. Evaporation of the extracts to dryness yielded 0.23 g of keto-aldehyde. This was dissolved in 20 ml absolute ethanol, after which 0.4 ml 40% trimethylbenzylammonium hydroxide ("TRITON B ™") was added. The mixture was warmed at about 40° C. under nitrogen for about 1 hour, after which saturated sodium chloride solution and ether were added. The ether layer was separated and the aqueous layer was extracted again twice with ether. The extracts were dried by anhydrous $Na_2SO_4$ evaporated to dryness. The dark brown residue was rapidly chromatographed on silica gel (20 g) with hexane/ethyl acetate 90:10. The product was obtained as an unstable oil (0.15 g, 69% yield. NMR ($CDCl_3$): δ0.95 (d, J=6, $\underline{CH_3}$CH), 3.77 (s, $CH_3O$), 5.35 (m, trans-CH=CH), 7.20 (m, proton at C-3).

EXAMPLE XVI - Step (d)

Preparation of dl-2-[(E)-6'-(m-methoxyphenyl)-2'-methyl-3'-hexenyl]-1-methyl-2-cyclopenten-1-ol (Formula I, $R_1=$methyl; $R_2=H$; $R_3=$hydroxy; $R_4$ methyl; $R_5$ methoxy)

The product from Example XV (0.142 g, 0.50 mmol) was dissolved in dry ether (10 ml) and cooled under nitrogen to about −70° C. A solution of methyl-lithium in ether (1.5 ml, 1 M, 3 eq.) was added and the resultant mixture was stired for about a further 10 minutes. A few drops of water were added, after which the reaction mixture was warmed to room temperature and dried with the aid of anhydrous $Na_2SO_4$. Filtration and evaporation under vacuum at less than about 20° C. gave 0.15 g product in the form of an unstable colorless oil. NMR ($CDCl_3+C_5D_5N$): $\delta 0.88$ and 0.95 ($2 \times d$, $J=6$, $\underline{CH}_3CH$), 1.25 and 1.29 ($2 \times s$, $CH_3$—C—OH), 3.75 (s, $CH_3O$), 5.2–5.6 (m, olefinic protons).

EXAMPLE XVII—Step (e), Cyclisation

Preparation of dl-1- and -3-methoxy-11α, 17-dimethyl-$\Delta^{1,3,5(10),13(17)}$-gonatetraene (Formula II and III, $R_4$=methyl; $R_5$=methoxy; $R_6$=methyl The product from Example XVI (0.15 g, 0.50 mmol) was cyclized with stannic chloride in dichloromethane at about −70° C. in the way described in Example IX, giving 15.6 mg (11% yield) of the 1-methoxy-isomer and 44.4 mg (31% yield) of the 3-methoxy-isomer. The products consisted of 85% and 80% respectively of the 11α-methyl isomer, which was isolated in the way described in Example IX.

EXAMPLE XVIII - Step (d)

Preparation of dl-2-[(E)-6′-(m-methoxyphenyl)-2′-methyl-3′-hexenyl]-1-ethyl-2-cyclopenten-1-ol (Formula I, $R_1$=ethyl; $R_2$=H; $R_3$=hydroxy; $R_4$=methyl; $R_5$=methoxy)

The cyclopentenone from Example XV is caused to react with ethyl-lithium in the way described in Example XVII to give the corresponding 1-ethyl-2-cyclopentenol.

EXAMPLE XIX—Step (e)

Preparation of dl-1- and -3-methoxy-11α-methyl-17-ethyl-$\Delta^{1,3,5(10),13(17)}$-gonatetraene (Formula II and III, $R_4$=methyl; $R_5$=methoxy; $R_6$=ethyl)

The 1-ethyl-2-cyclopentenol of Example XVIII was cyclized to the gonatetraene product named above in the exact way described in Example XVII.

EXAMPLE XX—Steps (a)-(d)

Preparation of dl-3-methyl-2-[(E)-6′-(m-methoxyphenyl)-2′-ethyl-3′-hexenyl]-2-cyclopentenol (Formula I, $R_1$=H; $R_2$=methyl; $R_3$=hydroxy; $R_4$=ethyl; $R_5$=methoxy)

In the way described in Example VI, 3-(m-methoxyphenyl) propyl-triphenylphosphonium bromide was first caused to react with phenyl-lithium to give the ylide of formula IV (X=P ($C_6H_5)_3$), after which the ylide was condensed with dl-2-ethyl-5,8-bis(ethylenedioxy)nonanal (obtained in the way described in the Examples II to V inclusive, starting from 1-(5-methyl-2-furyl)-pentan-3-one), followed by hydrolysis, cyclodehydration and reduction in the way described in Examples VII and VIII.

EXAMPLE XXI—Step (f)

Preparation of dl-(E)-1-(2-furyl)-3-methyl-7-(m-methoxyphenyl)-4-heptene (Formula X, $R_2$=H; $R_4$=methyl; $R_5$=methoxy)

In the way described in the last paragraph of Example I, dl-1-iodo-2-methyl-4-(2-furyl)butane (obtained by reducing the butanal of Example XII to the corresponding butanol, followed by conversion with methane-sulphonic acid chloride into the mesylate and reaction of the latter with lithium iodide) was converted with triphenylphosphine into dl-2-methyl-4-(2-furyl)-butyl-triphenylphosphonium iodide, which was converted with phenyl-lithium, in the way described in Example VI, into the ylide of formula IX ($R_2$=H; $R_4$=methyl; $Y=P(C_6H_5)_3$), followed by condensation of the ylide with 3-(m-methoxyphenyl)propanal, giving the product, which was identical with the product of Example XIII.

EXAMPLE XXII—Step (f)

Preparation of dl-(E)-1-(5-methyl-2-furyl)-3-methyl-7-(m-methoxyphenyl)-4-heptene (Formula X, $R_2$=methyl; $R_4$=methyl, $R_5$=methoxy)

In the way described in Example II, using lithium iodide instead of lithium bromide, dl-2-methyl-5-(3-iodobutyl)-furan was prepared, which was converted with triphenylphosphine, as described in the last paragraph of Example I, into dl-2-methyl-4-(5-methyl-2-furyl)-butyltriphenylphosphoniumiodide. (m.p. 133°–135° C.). This compound was converted with phenyl lithium, in the way as described in Example VI, into the ylide of formula IX ($R_2$=methyl, $R_4$=methyl, $Y=P(C_6H_{5/3})$), followed by condensation of the ylide with 3-(m-methoxyphenyl)propanal, giving the product in the form of an oil, NMR ($CDCl_3$): $\delta 0.97$ (d, $J=6.5$, $\underline{CH}_3CH$), 2.22 (s, $CH_3$ at furan), 3.77 (s, $CH_3O$), 5.33 (m, CH=CH), 5.80 (m, protons at furan).

EXAMPLE XXIII—Steps (h), (b)–(d)

Preparation of dl-3-methyl-2-[(E)-6′-(m-methoxyphenyl)-2′-methyl-3′-hexenyl]-2-cyclopentenol (Formula I, $R_1$=H; $R_2$=methyl; $R_3$=hydroxy; $R_4$=methyl; $R_5$=methoxy)

In the way described in the Examples XIV - XVI, the Wittig product from Example XXII was converted into the product, which was identical to the product of Example VIII.

It is claimed as the invention:

1. A cyclisation substrate compound of the formula:

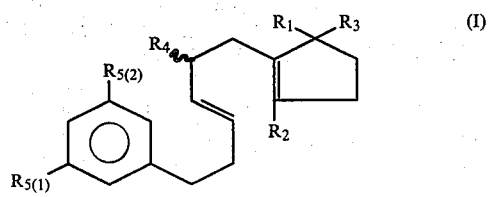

wherein:
(a) $R_1$ is H or alkyl of one to four carbons;
(b) $R_2$ is H or alkyl of one to four carbon atoms, with the proviso that $R_1$ is H when $R_2$ is alkyl, and with the proviso that $R_2$ is H when $R_1$ is alkyl;

(c) $R_3$ is a suitable leaving group selected from the group consisting of hydroxy, alkoxy of one to four carbons, alkoxyalkoxy of two to four carbons, acyloxy of one to about seven carbon atoms, and trialkysiloxy of less than fifteen carbons;

(d) $R_4$ is methyl; and (e) $R_{5(1)}$ and $R_{5(2)}$ are each H, alkyl of one to eight carbons, or optionally esterified or etherified hydroxy selected from the group consisting of hydroxy, alkoxy of one to four atoms, alkoxyalkoxy of two to four carbons, trialkylsilyloxy of one to fifteen carbons, cycloalkoxy of four to eight carbons, carboxyacyloxy of one to seven carbons, or heterocyclic ether of five to seven atoms and four to six carbons, with the proviso that at least one of $R_{5(1)}$ and $R_{5(2)}$ is hydrogen.

2. The compound of claim 1 wherein one of $R_1$ and $R_2$ is methyl or ethyl and the other is hydrogen.

3. The compound of claim 1 wherein $R_3$ is hydroxy or methoxy.

4. The compound of claim 1 wherein one of $R_{5(1)}$ and $R_{5(2)}$ is methyl or methoxy.

5. The compound of claim 1 wherein $R_1$ is H, $R_2$ is methyl, $R_3$ is OH, and one $R_{5(1)}$ and $R_{5(2)}$ is methoxy.

6. The compound of claim 1 wherein $R_1$ is methyl, $R_2$ is H, $R_3$ is OH, and one $R_{5(1)}$ and $R_{5(2)}$ is methoxy.

7. The compound of claim 1 wherein $R_1$ is ethyl, $R_2$ is H, $R_2$ is OH, and $R_3$ is methyl.

8. The compound of claim 1 wherein $R_1$ is H, $R_2$ is methyl, $R_3$ is hydroxy, and $R_5$ is methoxy.

9. A compound of the formula:

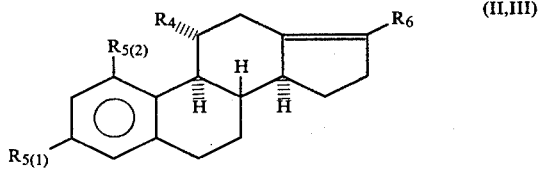

(II,III)

wherein:
(a) $R_4$ is methyl
(b) $R_{5(1)}$ and $R_{5(2)}$ are each H, alkyl of one to eight carbons, or an optionally esterified or etherified hydroxy group selected from the group consisting of hydroxy, alkoxy of one to four carbons, alkoxyalkoxy of two to four carbons, trialkylsilyloxy of one to fifteen carbons, cycloalkoxy of four to eight carbons, carboxyacyloxy of one to seven carbons, or heterocyclic ether of five to seven atoms and four to six carbon atoms, with the proviso that at least one of $R_{5(1)}$ and $R_{5(2)}$ is H;
(c) $R_6$ is an alkyl of one to about four carbon atoms.

10. The compound of claim 9 wherein one of $R_{5(1)}$ and $R_{5(2)}$ is methoxy.

11. The compound of claim 9 wherein $R_6$ is $CH_3$.

12. The compound of claim 9 wherein, one of $R_{5(1)}$ and $R_{5(2)}$ is methoxy and $R_6$ is methyl.

13. The compound of claim 9 wherein one of $R_{5(1)}$ and $R_{5(2)}$ is methoxy and $R_6$ is ethyl.

14. A method of preparing compounds of the formulae:

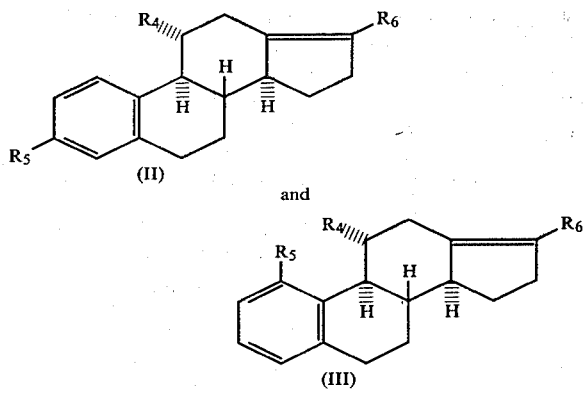

from the compound:

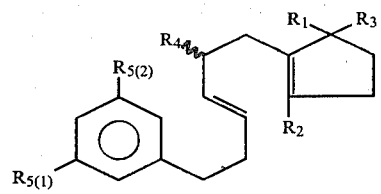

wherein:
(a) $R_1$ is H or alkyl of one to four carbon atoms;
(b) $R_2$ is H or alkyl of one to four carbon atoms, with the proviso that $R_1$ is H when $R_2$ is alkyl, and with the proviso that $R_2$ is H when $R_2$ is alkyl;
(c) $R_3$ is a suitable leaving group selected from the group consisting of hydroxy, alkoxy of one to four carbons, alkoxyalkoxy of two to four carbons, acyloxy of one to about seven carbons, and trialkylsilyloxy of less than fifteen carbons;
(d) $R_4$ is methyl; and
(e) $R_{5(1)}$ and $R_{5(2)}$ are each H, OH, alkyl of one to eight carbons, or optionally esterified hydroxy selected from the group consisting of hydroxy, alkoxy of two to four carbon atoms, alkoxyalkoxy of two to four carbons, trialkylsilyloxy of one to fifteen carbons, cycloalkoxy of four to eight carbons, carboxyacyloxy of one to seven carbons, or heterocyclic ether of five to seven atoms and four to six carbons, with the proviso that at least one of $R_{5(1)}$ and $R_{5(2)}$ is hydrogen;
$R_6$ is an alkyl of one to about four carbon atoms;
which comprises the step of:
cyclising compound I in a suitable solvent with an effective amount of one or more of the acids consisting of the suitable protic and suitable aprotic Lewis acids at a temperature below about room temperature and above about $-150°$ C.

15. The method of claim 14 wherein the cyclisation takes place from about $+10°$ C. to about $-100°$ C.

16. The method of claim 14 wherein an aprotic Lewis acid is used.

17. The method of claim 16 wherein the amount of Lewis acid employed is from about 0.5 to about 5 moles per mole compound (I).

18. The method of claim 14 wherein a protic Lewis acid is used.

19. The method of claim 18 wherein the protic Lewis acid employed has a $pK_{(20° C.)}$ of less than about 2.

20. A compound of the formula:

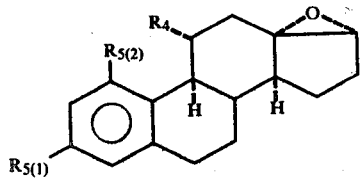

wherein $R_4$ is methyl and
$R_{5(1)}$ and $R_{5(2)}$ are each H, alkyl of one to eight carbons, or an optionally esterified or etherified hydroxy group selected from the group consisting of hydroxy, alkoxy of one to four carbons, trialkylsilyloxy of one to fifteen carbons, cycloalkoxy of four to eight carbons, carboacyloxy of one to seven carbons, or heterocyclic ether of five to seven atoms and four to six carbon atoms, with the proviso that at least one of $R_{5(1)}$ and $R_{5(2)}$ is H.

* * * * *